Figure 1:
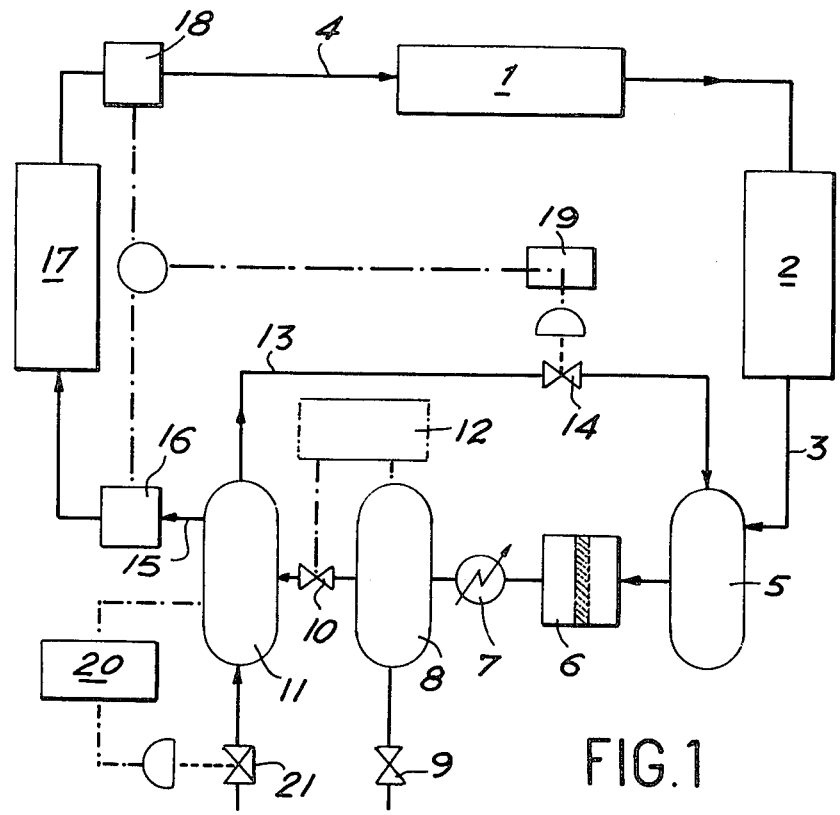

United States Patent [19]

Bonmati et al.

[11] 4,230,464
[45] Oct. 28, 1980

[54] METHOD FOR RECYCLING A CARRIER GAS FROM THE TRAPPING SYSTEM TO THE INLET OF A GAS CHROMATOGRAPHIC SEPARATION UNIT

[75] Inventors: Reynald Bonmati, New York, N.Y.; Bernard Roz, Brii sous Forges; Henri Tollet de Santerre, Lyons, both of France

[73] Assignees: Societe Nationale Elf Aquitaine, Paris; Societe de Recherches Techniques et Industrielles, Buc, both of France

[21] Appl. No.: 969,278

[22] Filed: Dec. 13, 1978

[30] Foreign Application Priority Data

Dec. 20, 1977 [FR] France .............................. 77 38393

[51] Int. Cl.² .......................................... B01D 15/08
[52] U.S. Cl. .......................................... 55/23; 55/67
[58] Field of Search ................. 55/23, 24, 26, 27, 67, 55/197

[56] References Cited

U.S. PATENT DOCUMENTS

| 3,357,157 | 12/1967 | O'Donnell | 55/23 |
| 3,455,817 | 7/1969 | Morell | 55/67 |
| 3,712,028 | 1/1973 | Deans | 55/197 X |

Primary Examiner—John Adee

[57] ABSTRACT

During the recycling operation, the carrier gas is subjected to a pre-purification prior to the conventional purification, the flow rate and the pressure of the carrier gas being maintained at strictly constant values at the inlet of the chromatographic unit. The method is primarily applicable to low-pressure gas chromatography and permits finer separations as well as higher productivity than atmospheric-pressure chromatography.

14 Claims, 2 Drawing Figures

METHOD FOR RECYCLING A CARRIER GAS FROM THE TRAPPING SYSTEM TO THE INLET OF A GAS CHROMATOGRAPHIC SEPARATION UNIT

This invention relates to a method for recycling a carrier gas from the trapping system to the inlet of a gas chromatographic separation unit, especially a unit of this type which operates at low pressure.

The method in accordance with the invention is particularly advantageous for recycling the carrier gas employed in a method of gas chromatography at low pressure as described in French patent Application No. 77 30694 filed on Oct. 12th, 1977 in the name of the present applicant. The method in accordance with the cited Application makes it possible to carry out finer separations than in conventional chromatography at atmospheric pressure while substantially reducing thermal shock in the case of thermodegradable products and consequently increasing productivity to a considerable extent. This method of low-pressure chromatography essentially consists in circulating a carrier gas and the gas mixture to be separated through a column packed with a suitable stationary phase, at low pressure, at high velocity, and at a temperature below the temperature of degradation of the products to be analyzed. In more precise terms, the pressure as measured at the exit of the column varies between 760 torr and 10 torr and preferably between 200 and 500 torr. The deoxygenated carrier gas can be either nitrogen, helium or hydrogen. The chromatographic column is filled with a porous substance of the "chromosorb" type (99% silica—1% alumina) impregnated with a conventional selective stationary phase such as those employed in analytical gas chromatography.

In a method of low-pressure chromatography of this type, it is clearly necessary to recycle the carrier gas. In fact, a column having a diameter of 400 mm of the type employed in the method of low-pressure chromatography utilizes during operation between 5 and 200 m³ per hour of hydrogen (or any other carrier gas). Under these conditions, discharge of the carrier gas into the atmosphere after use is inconceivable by reason of the cost of carrier gas which this would entail and also by reason of the atmospheric pollution which would result.

When carrying out a chromatographic process of this type, a certain number of disturbances are observed in the carrier gas flow rate as well as in the pressures at the inlet and outlet of the chromatographic column or columns. These disturbances can be caused by the injection, by slow or fast purges, and by orientation of the separated products towards one of the four to six trapping channels at the exit. However, in a method of gas chromatographic separation at low pressure, it is necessary to have a strictly constant cycle time; and this cycle time T is related to the molar flow rate G of carrier gas and to the pressures Pe and Ps at the column inlet and at the column outlet by the following relation:

$$T = k \times (Pe^3 - Ps^3)/G^2$$

Furthermore, it is necessary to ensure that the carrier gas is purified prior to reintroduction into the chromatographic unit. In fact, at the outlet of the chromatographic unit, the carrier gas contains a certain number of impurities such as hydrocarbons, traces of oxygen (which may have penetrated either through microleaks in the vacuum portion of the installation or which may arise from the presence of oxygen dissolved in the charge to be purified) and of water. In addition, the carrier gas may contain a few traces of the gases forming part of the initial gas mixture which it was desired to separate and which may have been entrained by said carrier gas.

The above-mentioned purification process can be performed by conventional means such as an association of activated charcoal for removing hydrocarbon molecules, a deoxygenation catalyst for removing traces of oxygen and finally a molecular sieve for the removal of water.

However, the carrier gas delivered by a low-pressure chromatography unit must be subjected to a much higher degree of purification than a carrier gas employed in an atmospheric-pressure chromatography unit; it is in fact known that, under conditions of constant operation of the trapping unit, the quantity of products derived from the initial mixture to be separated and remaining in the carrier gas is inversely proportional to the pressure at the outlet of the chromatographic column. It may thus be noted by way of example that, in the case of a pressure of 0.3 bar absolute and the same carrier gas flow rate, 3.3 times more products derived from the gas mixture to be separated will remain in the carrier gas of a low-pressure chromatography unit than in the carrier gas of an atmospheric-pressure chromatography unit.

Thus, recycling of the carrier gas employed in a chromatographic process, and more especially in a chromatographic process carried out at low pressure, gives rise to a certain number of problems.

The present invention is precisely directed to a method for recycling a carrier gas from the trapping system to the inlet of a gas chromatographic separation unit and makes it possible to solve these different problems.

The method in accordance with the invention essentially consists in subjecting the carrier gas during the recycling process to a pre-purification prior to a purification of conventional type and in maintaining the flow rate and pressure of said carrier gas at strictly constant values at the inlet of the chromatographic unit.

In accordance with a distinctive feature of the invention, in order to subject the carrier gas to the pre-purification process aforesaid after it has been withdrawn by suction from the outlet of the trapping system of the chromatographic unit, said carrier gas is compressed, then cooled and separated from the condensed products thus obtained. More specifically, in order to carry out said pre-purification of the carrier gas after this latter has been withdrawn by suction from the trapping system of the chromatographic unit into a so-called suction tank, said carrier gas is passed into a compressor, then into a heat exchanger and then into a condensation tank in which the carrier gas is separated from the condensed products thus obtained. This pre-purification is carried out in a constant manner while maintaining the pressure within the condensation tank at a constant value by making use of follow-up control and regulating means. In one embodiment of the invention, these follow-up and regulating means are constituted by a pressure detector which is placed on the condensation tank and transmits the information received to a regulating chain, whereupon said regulating chain acts on a valve placed at the outlet of the condensation tank.

In accordance with another distinctive feature of the method of the invention, in order to maintain the carrier gas flow rate at a strictly constant value at the inlet of the chromatographic unit and after said carrier gas has been pre-purified, one portion of the gas is fed back to the suction system placed at the outlet of the trapping system of the chromatographic unit and the other portion is passed to the inlet of the chromatographic unit. More specifically, in order to maintain the carrier gas flow rate at a strictly constant value and after said carrier gas has been pre-purified, it is collected in a so-called pre-purified carrier gas collecting tank. Then one portion of said carrier gas is withdrawn from said tank and fed back to the suction tank placed at the outlet of the trapping system of the chromatographic unit whilst the other portion is passed to the inlet of the chromatographic unit, said withdrawl and reintroduction of carrier gas being subjected to follow-up control and regulating means. In one embodiment of the method under consideration, the means for regulating and controlling said withdrawal and said reintroduction are constituted by a flow detector which is placed at the outlet of the pre-purified carrier gas collecting tank and transmits the information received to a regulating chain. Said regulating chain then produces action on a valve placed between the pre-purified carrier gas collecting tank and the suction tank.

In accordance with a further distinctive feature of the method of the invention, in order to maintain the carrier gas pressure at a strictly constant value at the inlet of the chromatographic unit, the pressure within the pre-purified carrier gas collecting tank is maintained constant by making use of follow-up control and regulating means. In one embodiment of the method, said follow-up control and regulating means are constituted by a pressure detector which is placed on the pre-purified carrier gas collecting tank and transmits the information received to a regulating chain. Said regulating chain then produces action on a three-way valve which puts the pre-purified carrier gas collecting tank into communication either with a reserve supply of carrier gas or with atmospheric air.

The carrier gas is constituted by a light gas such as hydrogen, helium, methane, nitrogen.

Figure 2:
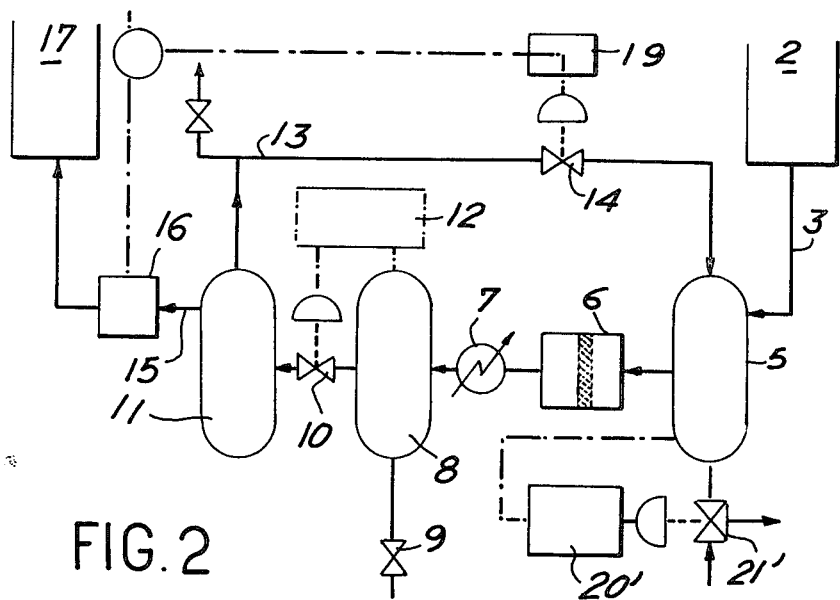

A more complete understanding of the invention will be gained from the following description, reference being made to the accompanying FIGS. 1 and 2 which are schematic illustrations of a device for the practical application of the method in accordance with the invention, said device being associated with the chromatographic unit from which the carrier gas is derived and into which it is to be reintroduced. In these figures, the different pipes are shown in full lines and electrical or pneumatic information is shown in chain-dotted lines.

In FIG. 1, the chromatographic unit is designated by the reference numeral 1 and the trapping system of said chromatographic unit is designated by the reference numeral 2. The exit carrier gas from the trapping system 2 has a pressure Ps at 3 and must necessarily have a pressure Pe at 4, that is to say prior to reintroduction into the chromatographic unit 1.

The carrier gas derived from the trapping system 2 is passed into the damping buffer tank 5, then into a compressor 6 having either one or a number of compression stages, depending on the desired discharge pressure. At the outlet of the compressor 6, the carrier gas which has undergone a substantial temperature rise is cooled within a heat exchanger 7, then passed into a tank 8. Settling of the condensed products thus obtained then takes place within said tank 8. These products represent a fraction of the impurities contained in the carrier gas, namely a fraction of the gaseous products of the starting mixture which it was desired to separate within the unit 1 and which have been entrained by the carrier gas. These condensed products are therefore removed from the tank 8 through the valve 9 whilst the carrier gas which has thus been pre-purified is passed into the damping tank 11 by means of the valve 10.

The theoretical quantity of products removed from the tank 9 is calculated as follows: if the gas leaves the trapping unit at a temperature in the vicinity of the cooling fluid temperature, said gas contains a molar fraction of residual products equal to $\pi t/Ps$ in which $\pi t$ represents the vapor pressure of the product to be purified at the temperature t and in which Ps represents the pressure at the exit of the traps, this pressure being substantially equal to the pressure at the exit of the chromatographic column or columns. The compressor 6 discharges the gas at a pressure Pr. If the carrier gas is again at the temperature t after cooling within the heat exchanger 7, it then contains only the molar fraction $\pi t/Pr$ of residual products. In consequence, $(Pr - Ps)/Pr \times 100\%$ of residual products are recovered.

In order to permit constant recovery of these residual products contained in the carrier gas and condensed within the tank 8, the pressure within said tank 8 is maintained constant; to this end, a pressure detector (not shown in the figure) is placed on the tank 8 and is intended to transmit the information received to a regulating chain 12 which then acts on the valve 10 in order to maintain the reference value established at the outset.

In order to maintain a constant flow rate of carrier gas at the inlet to the chromatographic unit 1, a fraction of the pre-purified carrier gas which has been collected in the tank 11 is withdrawn at 13 and reintroduced into the tank 5 through the valve 14; the other fraction of the pre-purified carrier gas collected in the tank 11 is passed via the line 15 to the inlet of the chromatographic unit 1.

The withdrawal of a fraction of pre-purified carrier gas at 13 and the reintroduction of this latter into the tank 5 are subjected to a follow-up control and regulating system. In fact, a flow detector is placed at the outlet of the tank 11, namely either at 16 upstream of the conventional purification system 17 or at 18 downstream of said system 17. Said flow detector delivers the information received to a regulating chain 19 in such a manner that a greater or lesser quantity of carrier gas is permitted to pass to the tank 5, depending on the reference value established beforehand. The other fraction of the pre-purified carrier gas which leaves the tank 11 at 15 is fed into the system 17 for conventional purification (activated charcoal, deoxygenation catalyst, molecular sieve), then leaves said system 17 and is passed to the inlet of the chromatographic unit 1.

Furthermore, in order to maintain the pressure of the carrier gas at a constant value at the inlet of the chromatographic unit, the pressure is maintained at a constant value within the tank 11. To this end, there is placed on the tank 11 a pressure detector (not shown in the figure) which transmits the information received to a regulating chain 20 and this latter then produces action on the three-way valve 21. Said valve communicates on the one hand with the tank 11 and on the other hand either with a reserve supply of carrier gas or with atmospheric air. Thus, depending on the pressure information received, either a make-up quantity of carrier gas is supplied or decompression is performed in order to reduce the pressure to the reference value.

It is thus apparent that, during recycling of the carrier gas, constant pre-purification of the carrier gas is carried out while at the same time maintaining the flow rate and the pressure of said carrier gas at the constant value desired at the inlet of the chromatographic unit.

The foregoing description relating to the execution of the method in accordance with the invention applied to recycling of a carrier gas employed in a method of gas chromatography at low pressure. However, the method according to the invention is not limited to recycling of a carrier gas derived from a chromatographic unit of this type and is equally applicable to recycling of the carrier gas employed in a chromatographic process carried out at atmospheric pressure. In this case the equipment and operation remain the same but the system for regulating the pressure of the carrier gas is placed on the tank 5. The accompanying FIG. 2 accordingly shows the regulating chain 20' which produces action on the three-way valve 21' according to the information supplied by the pressure detector placed on the tank 5 so that said valve accordingly puts this latter either in communication with a reserve supply of carrier gas or in communication with atmospheric air.

In the case of a chromatographic unit which operates at low pressure, this system for regulating the pressure of the carrier gas cannot be mounted on the tank 5 since this would clearly not be possible if it were desired to carry out decompression or pressure relief. It is for this reason that said regulating system is placed on the tank 11 in the embodiment shown in FIG. 1.

EXAMPLE 1

A method of separation of a gas mixture is carried out at atmospheric pressure in accordance with the diagram shown in FIG. 2, in a column having a diameter of 125 mm and having 700 plates. Under production conditions, 1.5 kg/h of an intermediate pharmaceutical product designated as "FB 235" and having 99.7% purity is obtained from a 91% charge; the flow rate of carrier gas consisting of hydrogen is 4 m$^3$ per hour. The operation takes place as follows:
Ps (pressure at outlet of column): 1.15 bar absolute
Pr (pressure at outlet of compressor 6): 5 bar absolute
Pe (pressure at inlet of column): 1.6 bar absolute.

In a first stage, the regulating chain 19 for controlling the carrier gas flow rate is inactive; the valve 21' for regulating the carrier gas pressure is isolated; and only the regulating chain 12 for constant pre-purification of the carrier gas is in operation. It is possible to observe variations of ±10% in the flow rate which are brought about by the trap valves of the chromatographic unit, and variations of −28% caused by injections at ten-second intervals in a cycle of 3 minutes 50 seconds.

A second stage consists in utilizing the method in accordance with the invention or in other words the system for automatic regulation of carrier gas flow rate and pressure while at the same time carrying out pre-purification of said carrier gas. The following results are thus obtained: at the optimum setting of the regulating chain 19, the variations are accordingly limited respectively to −4% in the case of the duration of injection and to ±2% in the case of changes in operating ranges.

Moreover, it has been possible to recover at 9, at the outlet of the tank 8, 42% of a liquid having a composition corresponding to that of the charge injected into the chromatographic unit.

EXAMPLE 2

A method of separation by chromatography at low pressure is carried out in accordance with the diagram shown in FIG. 1 with a carrier gas flow rate of 4 m$^3$ per hour. The operation takes place as follows:
Ps = 0.35 bar absolute
Pr = 5 bar absolute
Pe = 1.16 bar absolute.

In a first stage, when the regulating systems in accordance with the invention are not employed and when the trapping channel is changed at one-minute intervals, disturbances of +12% to −15% are observed in the flow rate, depending on the channels concerned.

In a second stage, when the regulating systems in accordance with the invention are put into operation, it is found that stabilization of these disturbances takes place at ±6.5%. Furthermore, the theoretical recovery at the outlet of the tank 8 is 93%.

What we claim is:
1. A method for recycling a carrier gas flowing from a gas chromatographic separation unit having an inlet and comprising a trapping system having an outlet which comprises:
 withdrawing the carrier gas from said trapping system,
 subjecting said carrier gas to a pre-purification step, then to a purification step,
 recycling gas purified in said purification step at the inlet of said chromatographic separation unit, and
 maintaining the flow rate and pressure of said carrier gas at strictly constant values at the inlet of said chromatographic unit.

2. A method according to claim 1, wherein said pre-purification step comprises compressing the carrier gas withdrawn from said trapping system, cooling the compressed carrier gas and separating the carrier gas from the condensed products thus obtained.

3. A method according to claim 2, wherein the carrier gas is withdrawn by suction from the outlet of the trapping system of the chromatographic unit into a suction tank, said carrier gas is passed into a compressor, then into a heat exchanger, and then into a condensation tank in which the carrier gas is separated from the condensed products thus obtained, and said separated carrier gas is passed from said condensation tank to a purification unit.

4. A method according to claim 3, wherein the pressure within the condensation tank is maintained at a constant value by follow-up control and regulating means.

5. A method according to claim 4, wherein said follow-up control and regulating means comprise a pressure detector which is placed on the condensation tank and transmits the information received to a regulating chain, whereupon said regulating chain acts on a valve placed at the outlet of said condensation tank, by which the carrier gas passes from said condensation tank to said purification unit.

6. A method according to claim 1, wherein maintaining the carrier gas flow rate at a strictly constant value at the inlet of the chromatographic unit is carried out by withdrawing one portion of the pre-purified gas, reintroducing said one portion of pre-purified gas with the carrier gas withdrawn from said trapping system, and passing the other portion of the pre-purified carrier gas to the inlet of said chromatographic unit.

7. A method according to claim 6, wherein said pre-purified carrier gas is collected in a so-called pre-purified carrier gas collecting tank whereupon one portion of said carrier gas is withdrawn from said tank and fed back to a suction tank placed at the outlet of the trapping system of the chromatographic unit whilst the other portion is passed to the inlet of the chromatographic unit, said withdrawal and reintroduction of pre-purified carrier gas being subjected to follow-up control and regulating means.

8. A method according to claim 7, wherein said follow-up control and regulating means comprise a flow detector which is placed at the outlet of the pre-purified carrier gas collecting tank, outlet by which outlet said pre-purified carrier gas is passed to the inlet of the chromatographic unit, and transmits the information received to a regulating chain, said regulating chain producing action on a valve placed between the pre-purified carrier gas collecting tank and the suction tank.

9. A method according to claim 1, wherein maintaining the carrier gas pressure at a strictly constant value at the inlet of the chromatographic unit is carried out by collecting the pre-purified carrier gas in a collecting tank and passing said collected gas to the inlet of said chromatographic column while maintaining the pressure within said collecting tank at a constant value by follow-up control and regulating means.

10. A method according to claim 9, wherein said follow-up control and regulating means comprise a pressure detector which is placed on said tank and transmits the information received to a regulating chain, said regulating chain producing action on a three-way valve which puts the pre-purified carrier gas collecting tank into communication either with a reserve supply of carrier gas or with atmospheric air.

11. A method according to claim 1, wherein maintaining the carrier gas pressure at a strictly constant value at the inlet of the chromatographic unit is carried out by withdrawing the carrier gas from said trapping system into a suction tank and feeding said withdrawn gas to a pre-purification unit, while maintaining the pressure within the suction tank at a constant value by follow-up control and regulating means.

12. A method according to claim 11, wherein said follow-up control and regulating means comprise a pressure detector which is placed on said suction tank and transmits the information received to a regulating chain, said regulating chain producing action on a three-way valve for putting the suction tank into communication either with a reserve supply of carrier gas or with atmospheric air.

13. A method according to claim 1, wherein the carrier gas is a gas selected from the group consisting of hydrogen, helium, methane, nitrogen.

14. A mathod according to any one of claims 1 to 13, wherein the chromatographic unit operates at low pressure.

* * * * *